United States Patent [19]
Loeffler et al.

[11] Patent Number: 6,001,640
[45] Date of Patent: Dec. 14, 1999

[54] VEGETABLE OIL ENZYMATIC DEGUMMING PROCESS BY MEANS OF ASPERGILLUS PHOSPHOLIPASE

[75] Inventors: Fridolin Loeffler, Bensheim; Hermann Plainer, Reinheim; Bruno Sproessler, Rossdorf; Hans Ottofrickenstein, Zwingenberg, all of Germany

[73] Assignees: Roehm GmbH, Darmstadt; Metallgesellschaft AG, Frankfurt am Main, both of Germany

[21] Appl. No.: 08/983,324

[22] PCT Filed: Jul. 4, 1996

[86] PCT No.: PCT/DE96/01190

§ 371 Date: Jan. 26, 1998

§ 102(e) Date: Jan. 26, 1998

[87] PCT Pub. No.: WO97/05219

PCT Pub. Date: Feb. 13, 1997

[30] Foreign Application Priority Data

Jul. 26, 1995 [DE] Germany .................. 195 27 274

[51] Int. Cl.$^6$ ........................................ C11C 1/00
[52] U.S. Cl. ................ 435/271; 435/267; 435/913; 435/917; 435/918
[58] Field of Search ................ 435/267, 256.1, 435/913, 917, 918, 271

[56] References Cited

U.S. PATENT DOCUMENTS

| | | | |
|---|---|---|---|
| 5,288,619 | 2/1994 | Brown et al. | 435/134 |
| 5,314,706 | 5/1994 | Colarow et al. | 426/605 |

FOREIGN PATENT DOCUMENTS

| | | | |
|---|---|---|---|
| 0 219 269 | 4/1987 | European Pat. Off. | C13K 1/08 |
| 0 513 709 A2 | 11/1992 | European Pat. Off. | C11B 3/00 |
| 0 575 133 A2 | 12/1993 | European Pat. Off. | C12N 9/16 |
| 0 622 446 A3 | 2/1995 | European Pat. Off. | C11B 3/00 |
| 61-289884 | 12/1986 | Japan . | |
| 4-356191 | 12/1992 | Japan . | |
| 4-356192 | 12/1992 | Japan . | |
| 6-327475 | 11/1994 | Japan . | |

OTHER PUBLICATIONS

Process Biochemistry, vol.I 30, No. 5, 1995.

*Primary Examiner*—David A. Redding
*Attorney, Agent, or Firm*—Oblon, Spivak, McClelland, Maier & Neustadt, P.C.

[57] ABSTRACT

A degumming step in the production of edible oils is disclosed. Vegetable oils from which hydratable phosphatides have preferably been eliminated by a previous aqueous degumming process, are freed from non-hydratable phosphatides by an enzymatic treatment, so that they may be physically refined. The main characteristic of the invention is the use of phospholipase from an Aspergillus strain. The process is gentle, economical and environment-friendly.

26 Claims, No Drawings

VEGETABLE OIL ENZYMATIC DEGUMMING PROCESS BY MEANS OF ASPERGILLUS PHOSPHOLIPASE

SPECIFICATION

Vegetable oil enzymatic degumming process by means of Aspergillus phospholipase.

1. Field of the Invention

The invention relates to the process step of degumming in the production of food oils, where plant oils from which hydratizable phosphatides were preferably removed, to a great extent, by means of prior aqueous degumming, are freed from non-hydratizable phosphatides by means of enzyme treatment, to such an extent that they can be subjected to physical refining. The process is gentle, low-cost and environmentally safe.

2. State of the Art

The recognized refining processes for the production of food oils of the highest quality generally comprise the process steps of degumming, de-acidification, as well as bleaching and deodorization. In recent times, great efforts have been made to make the degumming process, in particular, more efficient and cost-effective. The desired goal in this connection is to degum the oil to such an extent that it can subsequently be de-acidified by means of distillation. The latter distillative de-acidification process has the great advantage, as compared with the conventional process of de-acidification by means of neutralization, that no waste is produced. However, a prerequisite for implementing this process is a very low content of phosphatides, e.g. a phosphorus content of less than 15 ppm in the oil, preferably less than 10 ppm. A phosphorus content of <5 ppm is ideal.

The mucilage substances in plant oils consist primarily of mixtures of phosphatides, with the amount and composition being dependent on the type of oil seed and the method of obtaining the oil. The great majority of phosphatides can be separated from their micellar solutions by means of hydratization, and used for obtaining lecithin. This process is referred to as wet degumming. A small portion of phosphatides is not hydratizable and remains in the oil. The chemical nature of these "non-hydratizable phosphatides" (NHP) is not completely clear. Studies have shown that they consist of calcium and magnesium salts of phosphatide acids, in a proportion of more than 50% (see Hermann Pardun, Die Pflanzenlecithine [Plant lecithins], Verlag für chem. Industrie H. Ziolkowsky KG, Augsburg, 1988, page 181). The goal of conventional technical degumming processes is to remove the non-hydratizable phosphatides from the oil to the greatest extent possible. The usual processes applied at present include the "Superdegumming process" and the "Unidegumming" process of the Unilever company, the "Total Degumming ("TOP") process" of the Vandemoortele company, the "Alcon process" of the Lurgi company, and the "UF process" of the company Krupp Maschinentechnik GmbH. In many instances, traditional aqueous degumming for removing hydratizable phosphatides is integrated into these processes, or precedes them.

It is typical for all these degumming processes that only purely mechanical or physical-chemical processes are applied, and these are not always optimally suited for all oil qualities. The apparatus requirement and the energy expenditure of all these processes are great, and in addition, there is no guarantee that the low phosphorus contents required for subsequent de-acidification by distillation will be achieved.

In some of these degumming processes, acid treatment is used as the active principle. It is known that strong acid agents are suitable for post-degumming of oils pre-degummed with water (see Pardun, loc. cit., pages 185–189, or U.S. Pat. No. 4,698,185). Preferably, citric acid is used in this connection.

An effective enzymatic process for degumming is presented, for the first time, in the European patent application 0 513 709. Here, a food oil pre-degummed with water is emulsified with an aqueous solution of a phospholipase ($A_2$, $A_1$, B), and separated from this aqueous phase. After this process, the oil contains less than 5 ppm phosphorus and is suitable for subsequent de-acidification by distillation. Important process parameters are emulsification of the aqueous phase which contains the enzyme to droplets <10 micrometers, the addition of citrate to the aqueous solution, a temperature of 50 to 70 C, and a pH preferably between 4 and 6. This pH adjustment in the acid range is surprising, because the optimum pH of all known phospholipases is pH 8. The enzymatic degumming process was introduced in the food oil industry by the Lurgi company, as the "EnzyMax process."

In DE-A 43 39 556, as another variant of this process, the re-use of the enzyme is described, in that it is released from a used aqueous phase which contains mucilage by adding surfactants or solution mediators, and recovered as an essentially mucilage-free solution, which contains at least 10% of the enzyme originally used.

In the "EnzyMax process," the advantageous effect of the citric acid can be utilized for extensive degumming, specifically by means of citric acid treatment which precedes or follows the enzyme treatment. Simultaneous use of citric acid and enzyme is not possible.

From JP-A 2-153997, it is known to treat crude or pre-degummed oil with an enzyme which demonstrates phospholipase-A activity. This state of the art teaches that by using phospholipase A, the phosphatides are changed in such a way that they can be easily removed by adsorbents such as activated clay or fuller's earth. For example, in Examples 1 and 2 of three implementation examples, the enzyme treatment is combined with fuller's earth treatment. In the third example, fuller's earth is not used. Instead, here particularly large amounts of enzyme (2,000–20,000 units) are used in large amounts of water (100–1,000 weight-% with reference to the oil). This results in an oil-in-water emulsion. No teaching is given with regard to dispersion of the oil in the aqueous phase which contains the enzyme, adjustment of the pH, the additional use of citrate, or re-use of the enzyme.

In JP-A 2-49593, a similar enzyme treatment of oils is described, but it is aimed not at degumming of the oil but at obtaining lysolecithin. For this, adjusting specific pH values is superfluous.

The process according to EP-A 0 328 789 also involves the conversion of lecithin in soybean oil to lysolecithin, by means of phospholipase A, for the production of mayonnaise-like products.

EP-A 0 622 446 describes an enzymatic process for degumming of oils and fats, which comprises several process steps. After treatment with phospholipase, the enzyme solution is centrifuged off, the remaining oil is washed with water at a pH of 3–6, and finally it is treated with fuller's earth. It is characteristic in this connection that both during the enzyme treatment and during the washing step, large amounts of water are used, specifically 30–200 weight-% with reference to the oil used. Here again, oil-in-water emulsions are formed. This means increased apparatus requirements, because large volumes of liquids must be moved, and also higher energy and disposal costs. No teaching is given for pH adjustment of the aqueous enzyme solution.

Making the required amount of enzyme available for operation of an enzymatic process on a large technical scale is a specific problem in the case of phospholipase. Here, the available amount is limited. Phospholipase $A_1$ is not commercially available, phospholipase B is available only in laboratory amounts; sources are extracts from rat liver or Streptomyces cultures. Phospholipase $A_2$ occurs in snake, scorpion, and bee toxin.

None of these sources is suited for the production of technically relevant amounts of enzyme. The technical production method for phospholipase $A_2$ which is currently in use is extraction from pig pancreas glands. However, the occurrence of suitable pancreas glands is very limited worldwide, and can by no means be increased ad libitum. In addition, phospholipase is only a subordinate by-product in the extraction process. The main products are pancreas proteases, particularly trypsin, as well as pig insulin. It is estimated that the current commercial volume of phospholipase $A_2$—which can hardly be increased—would be sufficient for at most two to three oil mills, even if the enzyme were re-used in the process, as described in EP-A 0 513 709.

Therefore there is the need for a source which makes the enzyme available in unlimited amounts. According to the state of the art, technical enzymes are obtained in any desired amount from microorganisms, e.g. from fungi or bacteria. For phospholipases $A_1$, $A_2$, and B, no microorganism is currently known which produces the enzyme in a sufficient yield. Phospholipase $A_1$ was isolated from *Rhizopus arrhizus, Escherichia coli* and *Bacillus megaterium,* phospholipase B was isolated from *Penicillium notatum* and Streptomyces strains. Surprisingly, there is no indication in the literature that phospholipase $A_1$, $A_2$, or B can be isolated from Aspergillus.

In contrast, lysophospholipases which are obtained from *Aspergillus niger* are known from EP 0 219 269. Lysophospholipases—they are referred to here as phospholipase $L_1$ and $L_2$—possess a different specificity as compared to the phospholipases mentioned above, in that they are exclusively able to split monacyl phosphatides, such as lysolecithin, for example. Pure lysophospholipases are used in an entirely different field of foods technology, namely to improve the yield in wheat starch filtration.

Task

It is the task of the present invention to make available a gentle, environmentally safe and cost-effective process for reducing the content of components which contain phosphorus in vegetable oils, to a level which allows further treatment of the oil by means of distillative de-acidification, in other words to phosphorus contents of less than 15 ppm, preferably less than 10 ppm, in the best case less than 5 ppm. These requirements can be met by an enzymatic process.

For this, there is a need for a microbial source which makes it possible to produce the phospholipase enzyme in unlimited amounts. According to the state of the art, only enzymes with acyl-splitting specificity are usable for this purpose, namely phospholipase $A_1$, $A_2$, and B. In this connection, it is extremely advantageous to use an enzyme-producing microorganism which was introduced into the foods industry a long time ago and can therefore be used without reservations. Examples of this are various yeast strains such as *Kluyveromyces cerivisiae,* Bacillus strains such as *B. subtilis,* or *Aspergillus strains* such as *A. niger* or *oryzae.*

Another task which was not accomplished previously is to combine the advantageous effect of two known processes, namely acid treatment and enzyme treatment, in a single step.

Finally, there is the task of making do with the smallest possible amounts of enzyme and acid, in order to be able to structure the process in particularly efficient and economical manner.

Solution

The task is accomplished by means of a process for reducing the content of components which contain phosphorus in vegetable oils, their enzymatic reduction by means of acyl-splitting phospholipases, characterized in that an enzyme derived from Aspergillus is used.

The production of technical enzymes by means of the cultivation of Aspergillus strains is an important and highly developed field of biotechnology. For example, enzymes from *Aspergillus niger* and others are used on a large scale in the starch industry (amyloglucosidases), the fruit-juice industry (pectinases), and in the baked-goods industry (xylanases). Enzymes from Aspergillus, particularly *A. niger,* were introduced into the foods industry a long time ago, and are known to be safe. Phospholipases $A_1$, $A_2$, or B from this source are not known. The use of phospholipases of this origin in the degumming process is an important characteristic of the present invention. In the search for strains containing phospholipase, sufficient phospholipase $A_2$ activity was found in the products sold by the applicant, VERON® 191 and ROHAPECT® 7104. Higher activity levels result from the known screening method of strain improvement by means of mutation and selection for increased phospholipase activity (see W. Gerhartz, "Enzymes in Industry," VCH Verlagsgesellschaft mbH, 1990, page 35).

The specificity of the phospholipase obtained from this source can be varied and complex. Differing from phospholipase $A_2$ obtained from pancreas, according to the state of the art, which by definition only splits the acyl group at the $C_2$ atom of a phospholipid molecule, phospholipases from Aspergillus mostly contain different acyl-splitting specificities at the same time. For example, in addition to $A_1$ and $A_2$ specificity, lysophospholipase activity is also found. The E.C. numbers 3.1.1.32, 3.1.1.4, and 3.1.1.5 correspond to the stated enzyme specificities. Lysophospholipase (EC No. 3.1.1.5) is also referred to as phospholipase B; however, according to presentations in the literature (see Pardun, loc. cit., page 140), it is unclear whether or not a differentiation must be made between lysophospholipase and phospholipase B. Certainly they have the common feature that they are able to split lysolecithin further, specifically to glycerophosphoryl choline. In addition, phospholipase B is able to attach lecithin. Since the phospholipase according to the invention possesses these two specificities, namely both for the substrate lecithin and for the substrate lysolecithin, it could be referred to as phospholipase B. Pure lysophospholipases from Aspergillus which are only able to split lysolecithin, but not lecithin, are inactive in the present degumming process, particularly under the acidic reaction conditions, according to what the applicant has learned until now. This also holds true for phospholipases C and D, which do not split acyl.

Therefore the specificity for lecithin, in other words the phospholipase $A_1$ and/or $A_2$ activity—it is difficult to differentiate analytically between the two—is an essential characteristic of the enzyme according to the invention. The simultaneous presence of these different specificities could be a reason for the advantageous effect of the enzyme according to the invention. Although it must be referred to as a single enzyme in most cases, it possesses the effect of an enzyme complex.

When using the enzyme according to the invention, its degree of purification does not have any great significance.

For example, the fermentation liquid itself, the retentate obtained after ultrafiltration, which is richer in enzyme, or the enzyme protein precipitated from the latter, can be used.

It is certainly within the spirit of the invention to use an enzyme obtained from a production strain modified by gene technology, instead of from a conventional Aspergillus production strain. Gene technology now offers a great number of possibilities for cloning the gene required for formation of phospholipase from Aspergillus and expressing it in a high yield in a suitable host strain. Either Aspergillus strains or other fungus strains and even bacteria strains are possible host strains.

Depending on its degree of purity, the amounts of enzyme used can lie between 0.0001 and 1%, with reference to the oil to be degummed.

A great advantage and an unexpected effect of the enzymes used according to the invention is the activity required for degumming: It is extraordinarily low. While activities of approximately 1000 lecitase units (LU) per 1 liter of oil were used in the state of the art, when using phospholipase $A_2$ from pancreas (see Example 1 in EP-A 0 513 709), activities of only 5 to 50 LU per liter of oil are sufficient when using the enzymes according to the invention, under the conditions described above. If the reaction time is longer, even amounts of less than 5 LU per liter of oil will achieve their goal.

The lysophospholipase activity found in purified Aspergillus phospholipase is actually higher than phospholipase $A_2$ activity, specifically 1 to 100 times higher. This results in amounts of 5 to 5000 lysolecitase units (LLU) per liter of oil, preferably 50 to 1000 LLU. These activity data apply for degumming batches in the batch process. When re-using the enzyme, the amounts of enzyme which must be added, with reference to 1 liter of oil, are significantly lower, e.b. ⅕ to ¹⁄₁₀ of the values indicated above. These low amounts of enzyme make it possible to do without re-use of the enzyme.

It is possible to mix the Aspergillus phospholipase according to the invention with other acyl-splitting phospholipases, in targeted manner, for example with other phospholipases from Aspergillus or with phospholipase $A_2$ from pancreas. In the latter case, however, a pH which comes close to both optimum pH values must be adjusted, in other words approximately pH 3–5.

The use of phospholipase from Aspergillus surprisingly also makes it possible to accomplish other tasks that were stated. For example, it is possible to use the enzyme in a citric acid solution, to combine the effect of the enzyme with that of the citric acid. The use of an enzyme in relatively concentrated citric acid solutions is unusual. In enzymology, hardly any enzymes are known which are stable at such low pH values and actually possess their optimum effect here. One of the few examples of such a spectrum of properties is pepsin of the digestive tract. The enzyme is dissolved in a 1–20% citric acid solution. At the same time, pH values of pH<4, preferably pH<3 are adjusted. If 5% citric acid solutions are used, for example, a pH value of approximately 2.3 is obtained.

Instead of citric acid, lactic acid, acetic acid, fumaric acid, phosphoric acid, as well as other inorganic and organic acids can also be used. However, edible acids, particularly citric acid, are preferred. It should be noted that the phosphorus contents which can be achieved with acid solutions alone, in other words without using enzyme, are not sufficiently low, particularly in the case of pre-degummed oils.

The optimum pH value adjusted in the process according to the invention, at 2–3, does not agree with the optimum pH value found according to usual analytical methods. The latter is pH=8, where egg yolk as the substrate is emulsified in the enzyme solution at 40 C, and the activity is determined as a function of the pH value. The surprisingly low optimum pH for the process could be explained by the special conditions of the phase border surface, where perhaps a higher pH occurs than the one measured in the aqueous phase ("bulk phase").

The enzyme is intimately mixed with the oil in this acid aqueous solution. In this connection, every effort should be made to keep the aqueous phase as small as possible, in comparison with the oil phase, in order to keep the volumes which must be moved during subsequent separation as small as possible. As a rule, volumes of <10% relative to the oil phase are sufficient, and volumes of <5% are preferred. In every case, a water-in-oil emulsion is formed.

The oil phase to be treated can be soybean oil, sunflower oil, or canola oil. The former is the most important oil product. Other vegetable oils, such as linseed oil, coconut oil, or palm oil, as well as animal oils which contain disruptive phosphatides, can also be treated using the process according to the invention.

Since phospholipase would attack lecithin, it is not practical to use oils with a high lecithin content, such as crude soybean oil, in the process according to the invention. Starting substances are therefore pre-degummed, particularly water-degummed oils, which are generally characterized by a phosphorus content between 50 and 300 ppm. Only in exceptional cases do pre-degummed oils possess higher phosphorus contents, hardly ever higher than 500 ppm phosphorus.

Oils with varying quality can be processed on the same system. It is also possible to use partially degummed oils, as well as pressed oils and extraction oils, along with others, specifically in a mixture with pre-degummed oils. As an exception, the phosphorus content can then be above 500 ppm.

Previous drying of the oil is not necessary.

In order to be able to allow the enzyme to act, both phases, the oil phase and the aqueous phase which contains the enzyme, must be intimately mixed. It is by no means sufficient to merely stir them.

Good dispersion of the enzyme in the oil is guaranteed if it is dissolved in a small amount of water, 0.5–5 weight-% (relative to the oil), and emulsified in the oil in this form, to form droplets of less than 10 micrometers in diameter (weight average). Preferably, the droplets are smaller than 1 micrometer. Turbulent stirring with radial velocities above 100 cm/sec has proven itself. Instead, the oil can be circulated in the reactor using an external rotary pump. The aqueous phase containing the enzyme can also be finely dispersed by means of ultrasound action. A dispersion apparatus such as an Ultraturrax is usual.

The enzymatic reaction probably takes place at the border surface between the oil phase and the aqueous phase. It is the goal of all these measures for mixing to create the greatest possible surface for the aqueous phase which contains the enzyme. The addition of surfactants increases the microdispersion of the aqueous phase. In some cases, therefore, surfactants with HLB values above 9, such as Na-dodecyl sulfate, are added to the enzyme solution, as described in EP-A 0 513 709. A similar effective method for improving emulsification is the addition of lysolecithin. The amounts added can lie in the range of 0.001% to 1%, with reference to the oil. In all cases, highly dispersed water-in-oil emulsions are produced by the process according to the invention.

The temperature during enzyme treatment is not critical. Temperatures between 20 and 80 C are suitable, but the latter can only be applied for a short time. The phospholipase according to the invention is characterized, overall, by good temperature resistance. It is not impaired by the low application pH. Application temperatures of 30–50 C are optimal.

The treatment period depends on the temperature and can be kept shorter with an increasing temperature. Times of 0.1 to 10, preferably 1 to 5 hours are generally sufficient. The reaction takes place in a degumming reactor, which can be divided into stages, as described in DE-A 43 39 556. Therefore continuous operation is possible, along with batch operation. The reaction can be carried out in different temperature stages. For example, incubation can take place for 3 hours at 40 C, then for 1 hour at 60 C. If the reaction proceeds in stages, this also opens up the possibility of adjusting different pH values in the individual stages. For example, in the first stage the pH of the solution can be adjusted to 7, for example, and in a second stage to 2.5, by adding citric acid. In at least one stage, however, the pH of the enzyme solution must lie below 4, preferably below 3, according to the invention. If the pH was subsequently adjusted below this level according to the invention, a deterioration of effect was found. Therefore the citric acid is preferably added to the enzyme solution before the latter is mixed into the oil.

After completion of the enzyme treatment, the enzyme solution, together with the decomposition products of the NHP contained in it, can be separated from the oil phase, in batches or continuously, preferably by means of centrifugation. Since the enzymes are characterized by a high level of stability and the amount of the decomposition products contained in the solution is slight—they precipitate as sludge—the same aqueous enzyme phase can be used several times. There is also the possibility of freeing the enzyme of the sludge, in accordance with DE-A 43 39 556, so that an enzyme solution which is essentially free of sludge can be used again.

Using the process of degumming according to the invention, oils which contain less than 15 ppm phosphorus are obtained. The actual goal is phosphorus contents of less than 10 ppm; in the ideal case, they should be less than 5 ppm. With phosphorus contents below 10 ppm, further processing of the oil according to the process of distillative de-acidification is easily possible.

In the course of the process according to the invention, a number of other ions, such as magnesium, calcium, zinc, as well as iron, are removed from the oil to a great extent. Thanks to the low iron content which is achieved, in most cases below 0.1 ppm, the product possesses ideal prerequisites for good oxidation resistance during further processing and storage.

EXAMPLES

Example 1

500 g of wet-degummed soybean oil with a residual phosphorus content of 190 ppm is heated to 40 C in a round flask. 26 g water, in which 5 g citric acid and 0.19 g of a powdered enzyme preparation were dissolved, are added. The enzyme preparation comes from a production batch of an *Aspergillus niger* fermentation and contains 60 phospholipase units (=lecitase units, LU) per g. One lecitase unit (LU) is the amount of enzyme which releases 1 micromole fatty acid from egg yolk in one minute, at 40 C and pH=8. The enzyme preparation was also tested for lysophospholipase activity. 1001 lysophospholipase units (=lysolecitase units, LLU) were measured per gram. One lysolecitase unit is the amount of enzyme which releases 1 micromole fatty acid from a lysolecithin emulsion per minute, at 55 C and pH=4.5. The enzyme preparation, which did not undergo any special purification with regard to the phospholipase content, therefore contains not only phospholipase $A_2$ but also a remarkably high lysophospholipase activity, and could be referred to as phospholipase B.

The content of the round flask is intensively dispersed by means of an external rotary pump. During this process, the contents of the flask are circulated about once per minute. The aqueous phase is present in a particle size of less than 1 $\mu$m. At intervals of one hour, samples are taken and checked for phosphorus content. The following values were obtained:

| Time in hours | 0 | 2 | 4 | 6 | 20 |
|---|---|---|---|---|---|
| Phosphorus content in ppm | 190 | 81 | 27.9 | 5.4 | 4.2 |

The low phosphorus content of <10 ppm required for subsequent distillative de-acidification was achieved in 6 hours by the process according to the invention.

Comparison Test 1

The work is performed as in Example 1, but instead of the enzyme preparation, a corresponding amount of whey protein, in other words non-enzymatic protein, is added. The samples taken after the same treatment times as above show that the phosphorus content does not drop below 121 ppm as the result of enzyme-free treatment. Adding citric acid alone is therefore not sufficient. The oil obtained is not suited for distillative de-acidification.

| Time in hours | 0 | 2 | 4 | 6 | 20 |
|---|---|---|---|---|---|
| Phosphorus content in ppm | 190 | 152 | 128 | 123 | 121 |

Comparison Test 2

The work is performed as in Example 1, but instead of the phospholipase from Aspergillus, a pure commercial lysophospholipase (G-Zyme, from Enzyme Biosystems, USA, 1172 LLU per g) is used. It does not possess any phospholipase $A_2$ activity. The samples taken after the same treatment times as above show that the phosphorus content does not drop below 85 ppm when using lysophospholipase alone, under the stated conditions. The oil obtained is not suited for distillative de-acidification.

| Time in hours | 0 | 2 | 4 | 6 | 20 |
|---|---|---|---|---|---|
| Phosphorus content in ppm | 190 | 138 | 124 | 119 | 85 |

What is claimed is:

1. A process for reducing content of phosphorus-containing components in vegetable oils, which comprises subjecting one or more vegetable oils containing said phosphorus-containing components to a mixture of phospholipases obtained from Aspergillus, said phospholipase mixture, comprising:
    i) an enzyme having phospholipase $A_1$ activity, or an enzyme having phospholipase $A_2$ activity, or both; and
    ii) an enzyme having lysophospholipase activity.

2. The process of claim 1, wherein said mixture of phospholipases used to treat said vegetable oils containing said phosphorus-containing components are in a solution having a pH of less than 4.

3. The process of claim 2, wherein said enzyme solution has a pH of less than 3.

4. The process of claim 2, wherein said pH of said enzyme solution is adjusted with citric acid, whereby the mixture of phospholipases acts in the presence of said citric acid.

5. The process of claim 1, which is effected at a temperature of from about 20 to 80° C.

6. The process of claim 4, which is effected at a temperature of from about 30 to 50° C.

7. The process of claim 1, wherein said enzymes are is contained in an aqueous phase which is emulsified in oil to droplets with a size of less than 20 μm.

8. The process of claim 1, wherein a partially pre-degummed oil is used.

9. The process of claim 8, wherein said partially pre-degummed oil is a wet-degummed oil.

10. The process of claim 8, wherein said vegetable oils have a phosphorous content of from 50 to 500 ppm which reduced to less than 15 ppm.

11. The process of claim 10, wherein said phosphorus content is reduced to less than 10 ppm.

12. The process of claim 10, wherein said phosphorus content is reduced to less than 5 ppm.

13. The process of claim 1, wherein said one or more vegetable oils is soybean oil.

14. The process of claim 1, wherein said one or more vegetable oils is canola oil, sunflower oil, linseed oil, coconut oil or palm oil.

15. The process of claim 2, wherein said solution containing said mixture of phospholipases is an aqueous solution which is separated from the treated oil and re-used thereafter.

16. The process of claim 1, which is effected continuously.

17. The process of claim 1, which is effected in batches.

18. The process of claim 1, which further comprises simultaneously reducing iron content of the one or more vegetable oils with the phosphorus-containing components thereof.

19. The process of claim 1, wherein a water-in-oil emulsion is formed wherein a volume of aqueous phase of <10% relative to oil phase is used.

20. The process of claim 19, wherein a volume of aqueous phase of <5% relative to oil phase is used.

21. The process of claim 1, wherein said mixture of phospholipases is obtained from *A. niger*.

22. The process of claim 7, wherein said enzymes are contained in an aqueous phase which is emulsified in oil to droplets with a size of less than 10 μm.

23. The process of claim 22, wherein said droplets have a size of less than 1 μm.

24. The process of claim 1, which further comprises adding a surfactant having an HLB value of greater than 9 to said mixture of enzymes.

25. The process of claim 18, wherein said iron content is reduced to less than 0.1 ppm.

26. The process of claim 1, wherein E.C. numbers 3.1.1.32, 3.1.1.4, and 3.1.1.5, correspond to enzyme specifics of phospholipase $A_1$, phospholipase $A_2$, and lysophospholipase activities, respectively.

* * * * *